(12) United States Patent
Takaoka

(10) Patent No.: US 6,387,434 B1
(45) Date of Patent: May 14, 2002

(54) POWDER PRODUCTS OF GINKGO LEAVES AND THEIR MANUFACTURING PROCESS

(76) Inventor: Terumi Takaoka, 2225-1, Oh-azasunouchikou, Kawauchicho, Onsegun, Ehime-ken (JP)

(*) Notice: Subject to any disclaimer, the term of this patent is extended or adjusted under 35 U.S.C. 154(b) by 0 days.

(21) Appl. No.: 09/537,438

(22) Filed: Mar. 27, 2000

(51) Int. Cl.$^7$ ............................................. A23L 1/2165
(52) U.S. Cl. ....................... 426/615; 426/453; 426/465; 426/518; 426/638; 426/640
(58) Field of Search .................. 426/615, 638, 426/640, 518, 453, 465; 424/195.1

(56) References Cited

U.S. PATENT DOCUMENTS 4,526,796 A * 7/1985 Ashikawa .................. 426/640
5,744,187 A * 4/1998 Gaynor ........................ 426/615
6,128,831 A * 10/2000 Durance et al. ............. 426/638

FOREIGN PATENT DOCUMENTS

CN 1097564 * 1/1995

* cited by examiner

Primary Examiner—Helen Pratt
(74) Attorney, Agent, or Firm—Moonray Kojima

(57) ABSTRACT

This invention relates to powder products of ginkgo leaves and its manufacturing processes, which includes crushing ginkgo leaves capable of maintaining various effects like healing intestinal disorder, which are typical of fibrous material, including fiber or food fiber in good quantity and exhibiting good effects of improvement of bloodstream by flavonol compounds without decreasing the compounds contained in the ginkgo leaves, by the steps of drying ginkgo leaves which have been washed and sliced, and of obtaining a specific form of crushed leaves of ginkgo after drying.

7 Claims, 4 Drawing Sheets

POWDER PRODUCTS OF GINKGO LEAVES AND THEIR MANUFACTURING PROCESS

BACKGROUND OF THE INVENTION

1. Field of the Invention

This invention relates to powder products of ginkgo leaves and its manufacturing processes, which consist in crushing ginkgo leaves.

2. Description of the Prior Art

It has been recently found out that ginkgo leaves contain flavonol compounds, which are effective in improving the condition of bloodstream and their extracts are being used for a medical liquid or healthy food to heal various diseases (thrombosis, cerebral infarct, dementia, atopy and diabetes and so on), which are caused by the deterioration of the bloodstream.

However, when extracts obtained from ginkgo leaves are manufactured, not only less flavonol compounds are contained but also various effects like healing intestinal disorder, which are proper to the fibrous material cannot be obtained because no fibrous material is contained at all (See the sections of fiber and food fiber.).

SUMMARY OF THE INVENTION

The main object of this invention is to provide a manufacturing process of powder products of ginkgo leaves capable of maintaining various effects like healing intestinal disorder, which are typical of fibrous materials, containing fiber or food fiber in good quantity and exhibiting good effects of improvement of bloodstream by flavonol compounds without decreasing the compounds contained in the ginkgo leaves, by the steps of drying ginkgo leaves which have been washed and sliced, and obtaining a specific form of crushed leaves of ginkgo after drying.

Another object of this invention is to provide a manufacturing process of the powder products of ginkgo leaves which have nutriments proper to green-yellow vegetables in addition to the effects typical of ginkgo leaves by slicing green-yellow vegetables into the ginkgo leaves.

One of other objects of the present invention is to provide a manufacturing process of powder products of ginkgo leaves capable of greatly increasing contained fibrous material by using the whole part of the ginkgo leaves including the leave hilt.

Another object of the invention is to provide a manufacturing process of powder products of ginkgo leaves capable of maintaining a good quantity of nutriments contained in the kale by putting the above mentioned green-yellow vegetables into the kale.

Another object of this invention is to provide a powder product of ginkgo leaves, which have been made according to the manufacturing process of the above-mentioned powder product of ginkgo leaves.

Furthermore another object of this invention is clarified according to the examples specified below.

DESCRIPTION OF THE PREFERRED EMBODIMENT

The following drawing is one of the examples of the preferred embodiment according to the invention.

Figure 1:
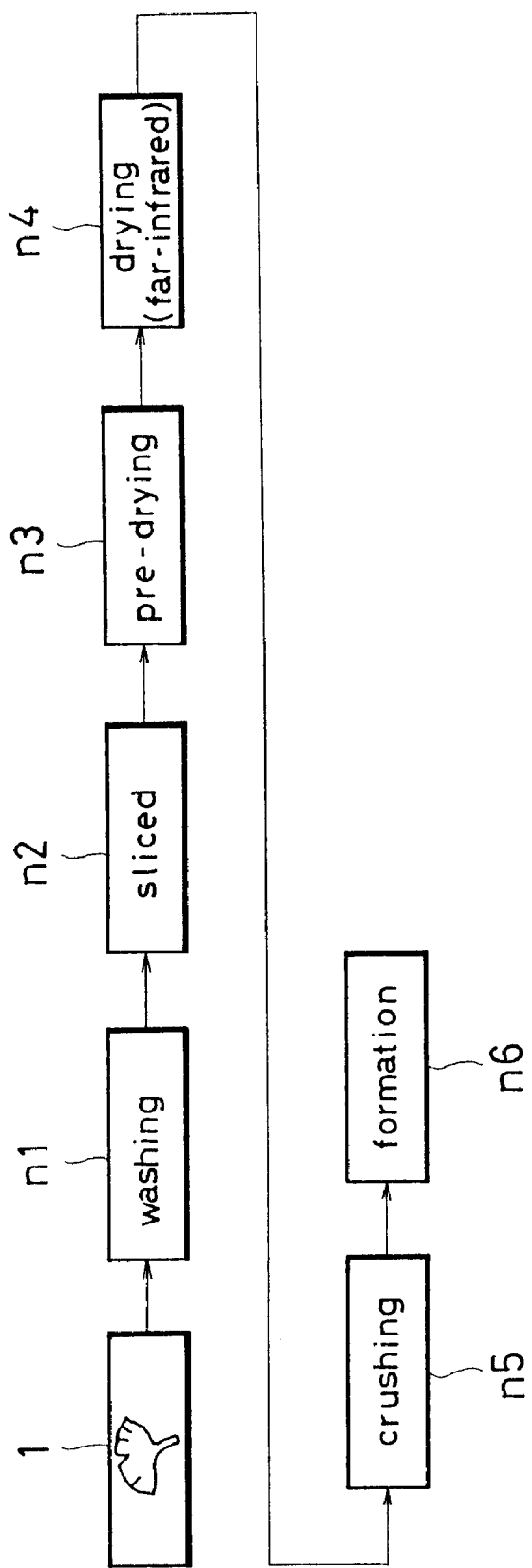
[FIG. 1] Step scheme showing powder products of ginkgo leaves and the manufacturing process in the present invention
Figure 2:
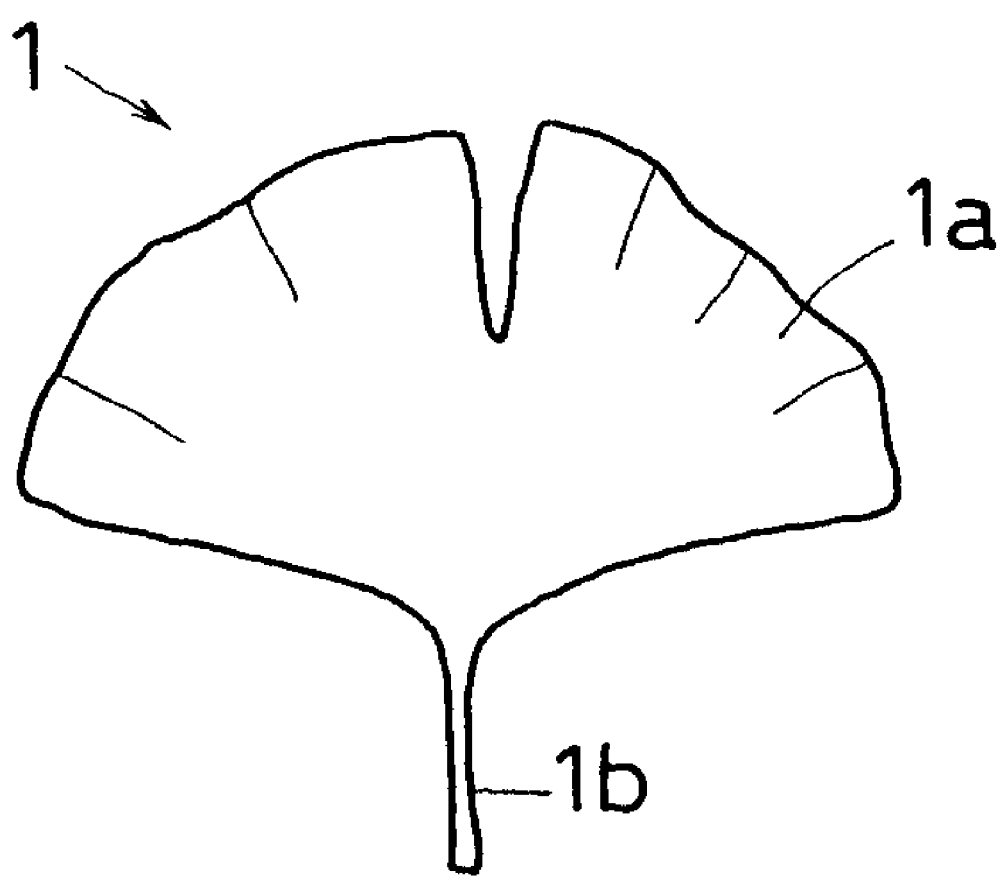
[FIG. 2] Explanatory drawing of the ginkgo leaves

The drawing shows powder products of ginkgo leaves and their manufacturing process. In the FIG. 1, a ginkgo leaf 1 is prepared at first. In this case, one leaf hilt 1b and one leaf 1a together with one leaf 1 as a whole are used without getting rid of a leaf hilt shown in the FIG. 2. It is preferable to use green leaves or young leaves before the said ginkgo leaves 1 turn into yellow. This is because, as ginkgo leaves turn into yellow, harmful ingredients will accumulate inside the leaves.

In the sterilizing and washing process n1, determined quantity of ginkgo leaves 1 is to be washed or sterilized. Accordingly when ginkgo leaves 1 are washed in the water containing approximately 200 ppm of hypophosphorous acid soda for 10 minutes, washing and sterilizing can be done simultaneously.

In the slicing process n 2, after sterilizing and washing ginkgo leaves 1 are sliced and minced using a slicing device.

In the preliminary drying process n 3, ginkgo leaves are pre-dried after slicing, in the temperature of about 46–50° C. for approximately 10–15 hours.

In the far-infrared drying step n 4, ginkgo leaves are irradiated by far-infrared for about 5–7 minutes after pre-drying and will be subjected to far-infrared drying and after that, ginkgo leaves pieces should contain approximately 3% water.

In the crushing step n 5, ginkgo leaves after infrared-drying will be crushed into the average of about 200 mesh by the crushing device so that they become powder.

In the forming step n 6, crushed ginkgo leaves powder will form solid pills or granules without being added an increasing agent at all. Otherwise they will be used in the form of powder.

Figure 3:
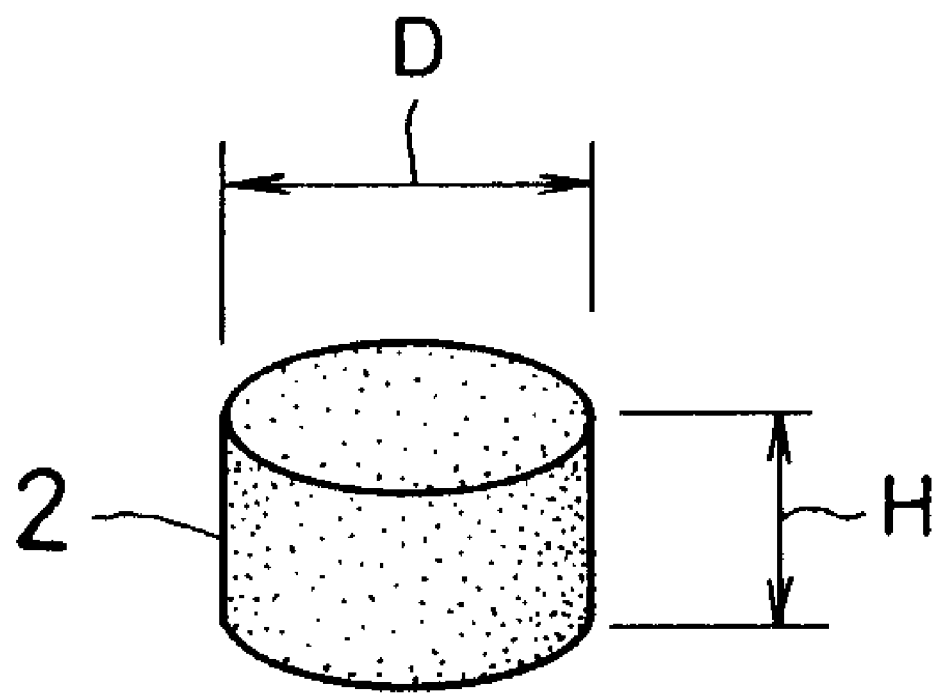
[FIG. 3] Enlarged drawing showing one example of the finished products

In this example, there will be formed a column granule of 100 mg, as in the FIG. 3, which has depth of 5 mm and height of 5 mm to produce the finished product 2. The form may be round or unbalanced triangle or other shapes and the finished product 2 will occasionally be wrapped.

According to the measurement of the contained flavonol compound (Flavonol is generally hydroxi derivatives of flavon which is described as $C^{15}H^{10}O^3$ and a flavonol compound here means quercetin-kaempherol-isorhamnetin.) and fiber and food fiber, the finished product 2 (which has not been added an increasing agent) has, inside 100 g of the finished product 2, approximately 244 mg of a flavonol compound, about 13.4 g of a fiber and about 35.9 g of food fiber.

Consequently, the manufacturing process of crushed products of ginkgo leaves described in the above example is provided with a washing step (the step n 1), slicing (the step n 2.) and the drying steps of the ginkgo leaves (the steps n 3, n 4), followed by a crushing of the ginkgo leaves after drying (the step n 5) to form a determined form of the said ginkgo leaves (powder and granule or pills) (the step n 6).

According to the above procedure, the flavonol compound contained in the ginkgo leaves 1 will not decrease. As it contains fibrous materials like fiber and food fiber in sufficient quantity, it will secure various effects of healing intestinal disorder, which is proper to the fibrous material, together with the improvement of bloodstream by flavonol compounds.

On the other hand, the above described ginkgo leaves 1 will use the whole part of the leaf hilt 1b.

According to the above procedure, it has become possible to produce the finished product 2 of the ginkgo leaves 1, in which the fibrous material contained therein has increased in large quantity.

Furthermore, the above example of the finished product 2 involving the ginkgo leaves has been made according to the above-specified manufacturing process.

According to the above procedure, flavonol compounds contained in the ginkgo leaves 1 will not decrease and as they contain fibrous materials like fiber and food fiber in high quantity they will be able to secure various effects of healing intestinal disorder, which is proper to the fibrous material, together with the improvement of bloodstream by flavonol compounds.

The above-described finished product 2 has both flavonol compounds of high quantity (approximately 244 mg) within 100 g and fibrous materials so that they are effective in improving thrombosis, cerebral infarct, dementia, atopy and diabetes. They are also effective in the sense they cure constipation, vein stream, paralysis of limbs, stiffening shoulders and arms and their pain and a chilly constitution in addition to the healing effects against callus and warts, which have been formed on the skin.

Figure 4:
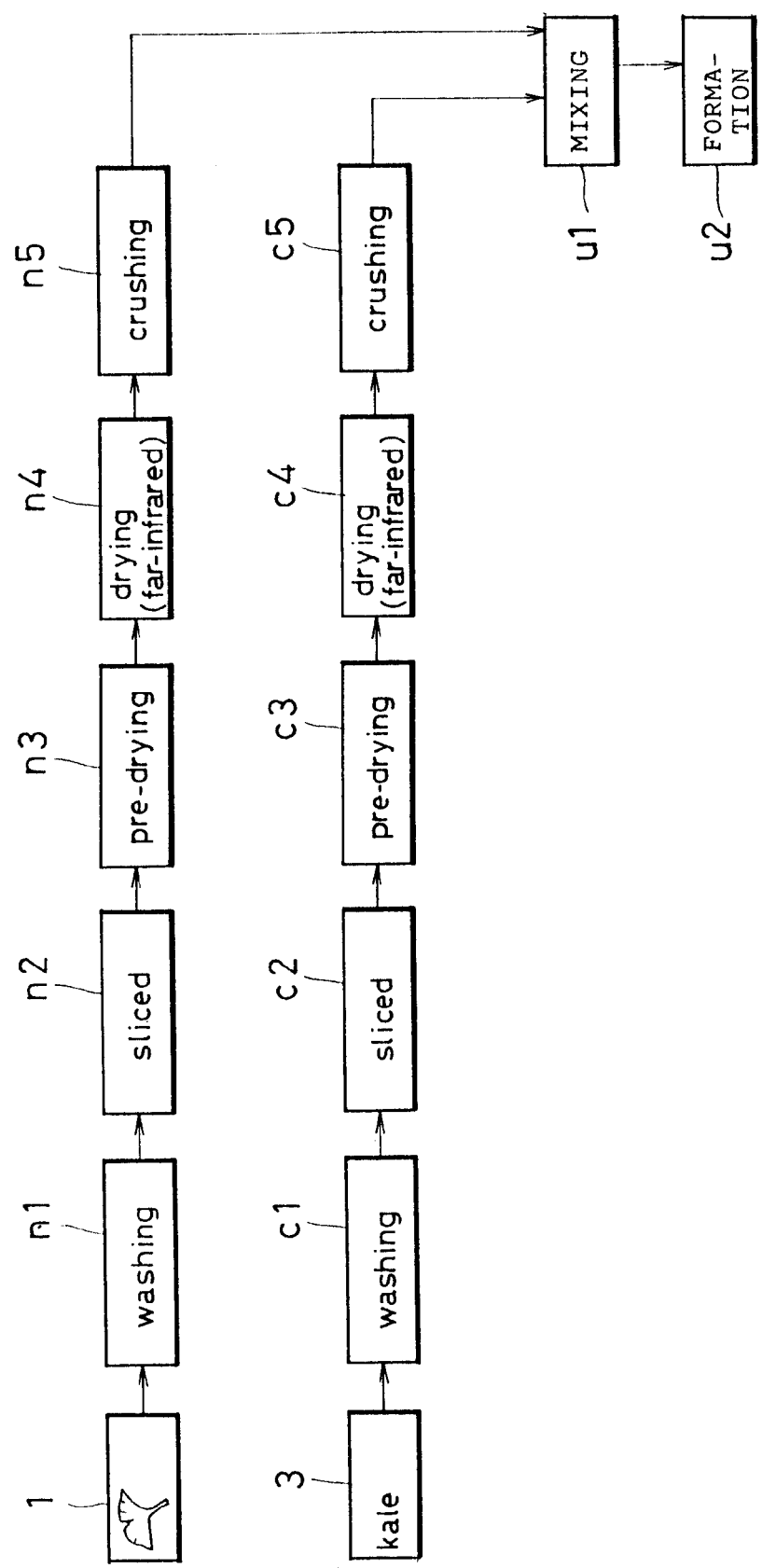
[FIG. 4] Step scheme showing other examples of the powder products of ginkgo leaves and other manufacturing processes in this invention

The FIG. 4 shows another example of powder products of the ginkgo leaves and their manufacturing process. In other words, according to the above-said example only ginkgo leaves 1 are used to produce a finished product 2, whereas according to the FIG. 4 in this example both ginkgo leaves 1 and green-yellow vegetables (for example, kale) are used to produce the finished product.

In this case, 20 wt % of ginkgo leaves 1 and 70–80wt % of green-yellow vegetables can be used but this rate of combination is not limitative.

According to the FIG. 4, at first ginkgo leaves 1 and kale as green-yellow vegetables 3 will each prepared. In respect of the process involving each step of n1–n5, the procedure is the same as in the foregoing examples.

Here is a detailed explanation of the procedure of kale 3 side. In the sterilizing and washing step C1, the 1% solution of citric acid as a sterilizer (Instead of citric acid solution, a solution containing hypophosphorous acid soda can be used.) may be first put into the kale 3 and washed for about 5 minutes. It is preferable to use outer leaves as kale 3. In the step 2, after kale 3 is rid of water drops upon sterilizing and washing, it will be sliced by the slicing device.

In the preliminary drying step c3, the pieces of kale after slicing will be pre-dried at the drying temperature of 45° C. for 8–12 hours in a drying condition.

In an infrared drying step c4, kale pieces will be irradiated by infrared ray for about 2–13 minutes in a middle temperature(approximately 45° C.) environment after pre-drying and will be infrared-dried. If it is necessary, kale pieces after being infrared-dried will be kept cold for a while and after that procedure kale pieces may be infrared-dried again. By this infrared-drying procedure it is possible to dry kale 3 without removing a high degree of nutriments.

In the crushing step c5, kale pieces are made into powders by the crusher, which crushes the kale into about 200 meshes as in the case with ginkgo leaves 1 after infrared-dry.

In the following mixing step U1, ginkgo leaves powders finished by each step of n1–n5 and kale powders finished by each step of c1–c5 are mixed almost evenly.

In the forming step U2, powders after the mixing procedure will be formed into granule or grain form or pills without being added any increasing agent at all or will be used in the form of powders. The finished product, which has gone through the process in the forming step n2, may be packaged, canned and bottled or accordingly wrapped, however, may each be wrapped for one stick-type bag or may be wrapped once for the several uses.

Such a finished product made as in the above steps (which has not been added increasing agents.) is provided with flavonol compounds contained in the ginkgo leaves 1 and fibrous materials like fiber and food fiber, together with a good deal of nutriments comprised in kale 3 like vitamin E, vitamin A, vitamin B1, vitamin B2, iron, potassium, phosphorous, calcium and food fiber (the general denomination of the food elements which cannot be digested by the digestive enzyme.).

According to the example shown in the FIG. 4, consequently, as the above ginkgo leaves are mixed with sliced pieces of vegetables (See kale pieces.) which are sliced (See the step c 2.) green-yellow vegetables (See kale 3.), it is possible to produce powder products of ginkgo leaves provided with nutriments of green-yellow vegetables (See kale 3.).

Furthermore, when the above green-yellow vegetables are put into kale 3 (the original type of cabbage), it is possible to produce powder products of ginkgo leaves, which are provided with a good deal of nutriments contained in the kale 3.

Instead of the above kale 3 other green-yellow vegetables like cabbage and lettuce may be used. The number shown in the above examples like process temperature, process time and mixing rate is only an example and not limitative.

What is claimed is:

1. A method of manufacturing a ginko product, comprising the steps of:

sterilizing and washing entire leaves of ginko including the hilts thereof;

slicing the sterilized and washed ginko leaves including the hilts thereof into a plurality of slices;

pre-drying the plurality of slices of ginko leaves at a temperature in the range of 45 to 50° C. for a period of 10 to 15 hours;

drying the pre-dried plurality of slices of ginko leaves with far-infrared radiation for a period of about 5 to 7 minutes so that said plurality of slices of ginko leaves contains about 3% moisture;

crushing the dried plurality of slices of ginko leaves to pieces having a size of about 200 mesh; and forming a granular or solid product from the crushed ginko leaves.

2. The method of claim 1, wherein said sterilizing and washing is with water containing about 200 ppm hybrophosphorous acid soda and for a period of about 10 minutes.

3. The method of claim 1, wherein said granules are about 100 mg in weight, and said solid product is about 5 mm in diameter and 5 mm in height.

4. The method of claim 1, wherein said granular or solid product with a 100 g weight comprises about 244 mg of flavonol component, about 13.4 g of fiber, and 35.9 g of food fiber.

5. The method of claim 1, further comprising the steps of:

sterilizing and washing a green-yellow vegetable;

slicing the sterilized and washed vegetable into a plurality of slices;

pre-drying the plurality of slices of vegetables at about 45° C. for about 8 to 12 hours;
drying the pre-dried plurality of slices of vegetables by infrared radiation at about 45° C. for about 2 to 13 minutes;
crushing the dried plurality of slices of vegetables; and
mixing the crushed ginko leaves and the crushed vegetables and forming granular or solid products thereof.

6. The method of claim 5, wherein said sterilizing and washing of said vegetable is in a 1% citric acid solution for about 5 minutes.

7. The method of claim 6, wherein said crushing of said vegetable results in pieces thereof of 200 mesh size.

* * * * *